United States Patent [19]

Lee et al.

[11] Patent Number: 4,681,621

[45] Date of Patent: Jul. 21, 1987

[54] HERBICIDAL 2-(2-SUBSTITUTED BENZOYL)-1,3-CYCLOPENTANEDIONES

[75] Inventors: David L. Lee, Martinez; William J. Michaely, Richmond, both of Calif.

[73] Assignee: Stauffer Chemical Company, Westport, Conn.

[21] Appl. No.: 804,027

[22] Filed: Dec. 3, 1985

Related U.S. Application Data

[63] Continuation of Ser. No. 683,883, Dec. 20, 1984, abandoned.

[51] Int. Cl.[4] .................. A01N 41/10; A01N 33/20
[52] U.S. Cl. .................................... 71/103; 71/98; 71/105; 71/107; 71/111; 71/122; 71/123; 558/396; 558/397; 558/412; 558/413; 558/414; 558/415; 560/9; 560/11; 560/12; 560/18; 560/21; 560/52; 564/85; 564/87; 564/88; 564/305; 564/440; 564/441; 564/442; 564/443; 568/29; 568/30; 568/31; 568/36; 568/37; 568/42; 568/43; 568/330
[58] Field of Search ............... 558/412, 396, 397, 413, 558/414, 415; 568/330, 31, 29, 30, 36, 37, 42, 43; 71/105, 122, 123, 98, 103, 107, 111; 564/85, 87, 88, 305, 440, 441, 442, 443; 560/9, 11, 12, 18, 21, 52

[56] References Cited

FOREIGN PATENT DOCUMENTS 0090262 10/1983 European Pat. Off. .

Primary Examiner—Dolph H. Torrence
Attorney, Agent, or Firm—Edwin H. Baker

[57] ABSTRACT

Compounds of the formula

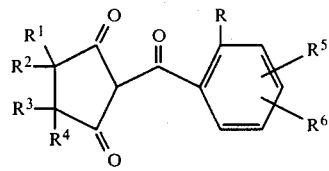

wherein R is halogen, preferably chlorine or bromine; $C_1$–$C_4$ alkoxy, preferably methoxy; nitro; cyano; —S-$(O)_nR'$ wherein n is the integer 0, 1 or 2, preferably 2 and R' is $C_1$–$C_4$ alkyl, preferably methyl; or R is $C_1$–$C_4$ alkyl or methyl and most preferably R is chlorine, bromine, methoxy, nitro, methyl or $CF_3$; $R^1$ is hydrogen or $C_1$–$C_4$ alkyl; $R^2$ is hydrogen, $C_1$–$C_4$ alkyl or

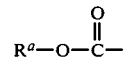

wherein $R^a$ is $C_1$–$C_4$ alkyl; $R^1$ and $R^2$ together are alkylene having 3 to 6 carbon atoms; $R^3$ is hydrogen or $C_1$–$C_4$ alkyl; $R^4$ is hydrogen or $C_1$–$C_4$ alkyl; and $R^5$ and $R^6$ independently are (1) hydrogen; (2) halogen; (3) $C_1$–$C_4$ alkyl; (4) $C_1$–$C_4$ alkoxy; (5) $OCF_3$; (6) cyano; (7) nitro; (8) $C_1$–$C_4$ haloalkyl; (9) $R^bSO_n$— wherein n is the integer 0, 1, or 2; and $R^b$ is (a) $C_1$–$C_4$ alkyl; (b) $C_1$–$C_4$ alkyl substituted with halogen or cyano; (c) phenyl; or (d) benzyl; (10) —$NR^cR^d$ wherein $R^c$ and $R^d$ independently are hydrogen or $C_1$–$C_4$ alkyl; (11) $R^eC(O)$— wherein $R^e$ is $C_1$–$C_4$ alkyl or $C_1$–$C_4$ alkoxy; or (12) $SO_2NR^cR^d$ wherein $R^c$ and $R^d$ are as defined are effective as herbicides.

14 Claims, No Drawings

HERBICIDAL 2-(2-SUBSTITUTED BENZOYL)-1,3-CYCLOPENTANEDIONES

This is a continuation of application Ser. No 683,883, filed Dec. 20, 1984, now abandoned.

BACKGROUND OF THE INVENTION

Compounds having the structural formula

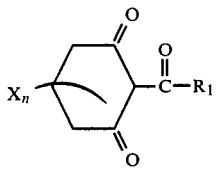

wherein X can be alkyl, n can be 0, 1, or 2, and $R_1$ can be phenyl or substituted phenyl are described in Japanese Patent Application 84632-1974 as being intermediates for the preparation of herbicidal compounds of the formula

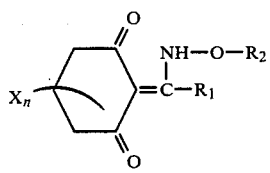

wherein $R_1$, X, and n are as defined above and $R_2$ is alkyl, alkenyl, or alkynyl. Specifically taught herbicidal compounds of this latter group are those where n is 2, X is 5,5-dimethyl, $R_2$ is allyl and $R_1$ is phenyl, 4-chlorophenyl or 4-methoyxphenyl.

The precursor intermediates for these three specifically taught compounds have no or almost no herbicidal activity.

European Patent Application No. 83 102 599.4 was published October 5, 1983 and relates to certain novel 2-(2-substituted benzoyl)-cyclohexane-1,3-diones as herbicides. The compounds have the following structural formula

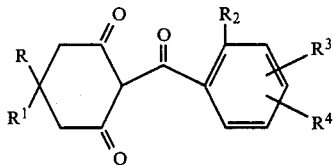

wherein R and $R^1$ are hydrogen or $C_1$-$C_4$ alkyl; $R^2$ is chlorine, bromine, or iodine; $R^3$ is hydrogen or halogen; and $R^4$ is hydrogen, chlorine, bromine, iodine, $C_1$-$C_4$ alkyl, $C_1$-$C_4$ alkoxy, nitro or trifluoromethyl.

In contrast to the teaching of the cited Japanese patent application, the compounds of this invention have exceptional herbicidal activity. Applicant's compounds must have the recited substitution in the 2-position of the phenyl moiety of their compounds to obtain the exceptional herbicidal activity. The exact reason why this substitution imparts exceptional herbicidal activity to the compounds is not fully understood.

DESCRIPTION OF THE INVENTION

This invention relates to certain novel 2-(2'-substituted benzoyl)cyclopentane-1,3-diones as herbicides. The compounds of this invention have the following structural formula

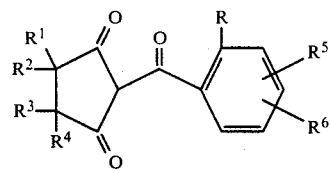

wherein

R is halogen, preferably chlorine or bromine, $C_1$-$C_4$ alkoxy, preferably methoxy; nitro; cyano; —S(O)$_n$R' wherein n is the integer 0, 1 or 2, preferably 2 and R' is ($C_1$-$C_4$ alkyl, preferably methyl; or R is $C_1$-$C_4$ alkyl, optionally substituted with halogen, preferably methyl; or $CF_3$ and most preferably R is chlorine, bromine, methoxy, nitro, methyl, $CF_3$ or $SO_2CH_3$;

$R^1$ is hydrogen or $C_1$-$C_4$ alkyl, preferably $C_1$-$C_2$ alkyl, more preferably methyl, most preferably $R^1$ is hydrogen or methyl;

$R^2$ is hydrogen; $C_1$-$C_4$ alkyl, preferably $C_1$-$C_2$ alkyl, more preferably methyl or

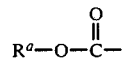

wherein $R^a$ is $C_1$-$C_4$ alkyl, most preferably $R^2$ is hydrogen or methyl; or $R^1$ and $R^2$ together are alkylene having 3 to 6 carbon atoms;

$R^3$ is hydrogen or $C_1$-$C_4$ alkyl, preferably $C_1$-$C_2$ alkyl, more preferably methyl; most preferably $R^3$ is hydrogen or methyl;

$R^4$ is hydrogen or $C_1$-$C_4$ alkyl, preferably $C_1$-$C_2$ alkyl, more preferably methyl; most preferably $R^4$ is hydrogen or methyl;

$R^5$ and $R^6$ independently are (1) hydrogen; (2) halogen, preferably chlorine, fluorine or bromine; (3) $C_1$-$C_4$ alkyl, preferably methyl; (4) $C_1$-$C_4$ alkoxy, preferably methoxy; (5) $OCF_3$; (6) cyano; (7) nitro; (8) $C_1$-$C_4$ haloalkyl, more preferably trifluoromethyl; (9) $R^bSO_n$— wherein n is the integer 0, 1 or 2, preferably 2; and $R^b$ is (a) $C_1$-$C_4$ alkyl, preferably methyl;

(b) $C_1$-$C_4$ alkyl substituted with halogen or cyano, preferably chloromethyl, trifluoromethyl or cyanomethyl;

(c) phenyl; or (d) benzyl;

(10) —NR$^c$R$^d$ wherein

R$^c$ and R$^d$ independently are hydrogen or $C_1$-$C_4$ alkyl;

(11) R$^e$C(O)— wherein

R$^e$ is $C_1$-$C_4$ alkyl or $C_1$-$C_4$ alkoxy; or

(12) —SO$_2$NR$^c$R$^d$ wherein R$^c$ and R$^d$ are as defined.

Preferably, $R^5$ is in the 3-position and $R^6$ is in the 4-position. Most preferably $R^5$ is hydrogen, chlorine, methoxy or methylthio and $R^6$ is hydrogen, chlorine, bromine, fluorine, $CF_3$, or $R^bSO_2$ wherein $R^b$ is $C_1$-$C_4$ alkyl, preferably methyl.

The term "halogen" is intended to mean chlorine, bromine, iodine or fluorine.

Salts of the above-described compounds (as defined hereinafter) are also the subject of the instant invention.

The compounds of this invention can have the following four structural formulae because of tautomerism:

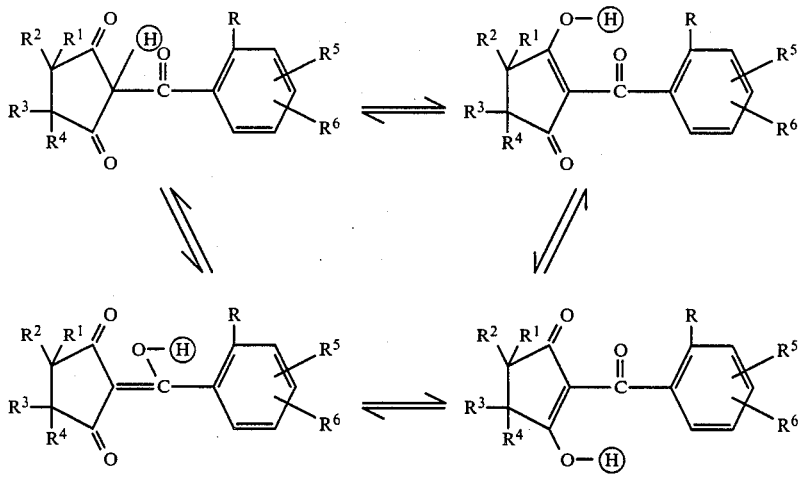

wherein R, $R^1$, $R^2$, $R^3$, $R^4$, $R^5$, and $R^6$ are defined above

The circled proton on each of the four tautomers is reasonably labile. These protons are acidic and can be removed by any base to give a salt having an anion of the following four resonance forms:

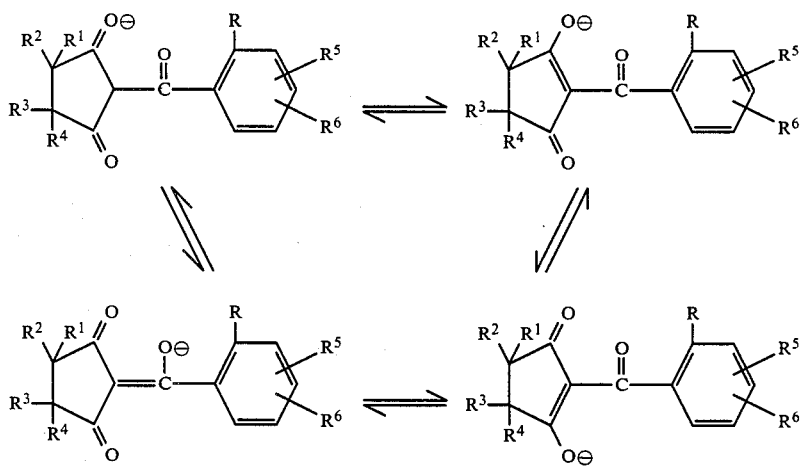

wherein R, $R^1$, $R^2$, $R^3$, $R^4$, $R^5$, and $R^6$ are as defined.

Examples of cations of these bases are inorganic cations such as alkali metals e.g. lithium, sodium, and potassium organic cations such as substituted ammonium, sulfonium or phosphonium wherein the substitutent is an aliphatic or aromatic group.

The compounds of this invention and their salts are active herbicides of a general type. That is, they are herbicidally effective against a wide range of plant species. The method of controlling undesirable vegetation of the present invention comprises applying an herbicidally effective amount of the above-described compounds to the area where control is desired.

The compounds of the present invention can be prepared by the following general method.

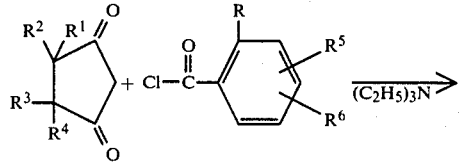

Generally, in step (1) mole amounts of the dione and substituted benzoyl chloride are used, along with a slight mole excess of triethylamine. The two reactants are combined in a solvent such as methylene chloride. The triethylamine is slowly added to the reaction mixture with cooling. The mixture is stirred at room temperature for several hours.

The reaction product is worked up by conventional techniques.

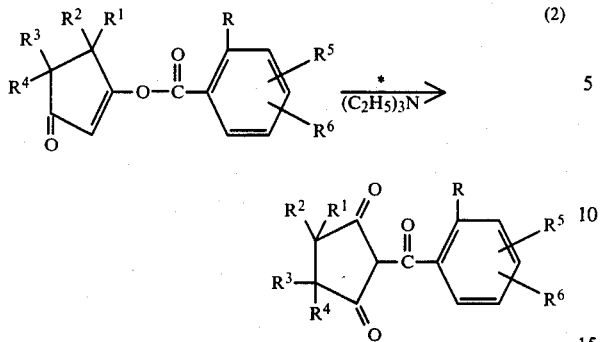

(2)

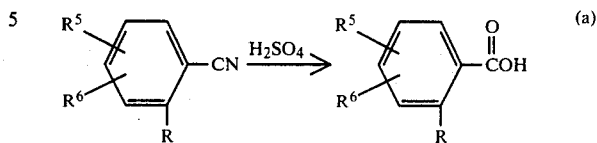

(a)

wherein R, $R^5$ and $R^6$ are as previously defined except that n is only zero and R is not cyano.

In reaction (a) the substituted benzonitrile is heated to reflux in aqueous sulfuric acid for several hours. The mixture is cooled and the reaction product is isolated by conventional techniques.

Generally, in step (2) a mole of the enol ester intermediate is reacted with 1 to 4 moles of the triethylamine, preferably 2 moles of the triethylamine and up to 0.5 mole, preferably 0.1 mole of a cyanide source (e.g., potassium cyanide or acetonecyanohydrin). The mixture is stirred in a reaction pot for about one hour at room temperature and the desired product is recovered by conventional techniques.

Alternatively, the desired compounds can be obtained via the following procedure.

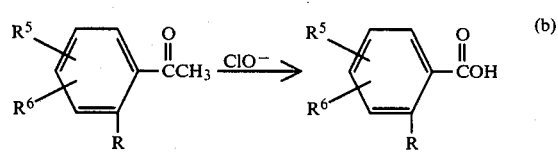

(b)

wherein R, $R^5$ and $R^6$ are as previously defined except that n is only zero.

In reaction (b) the substituted acetophenone is heated to reflux for several hours in an aqueous hypochlorite solution. The mixture is cooled and the reaction product is isolated by conventional techniques.

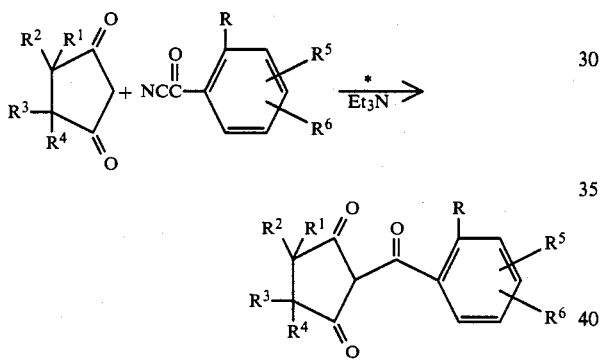

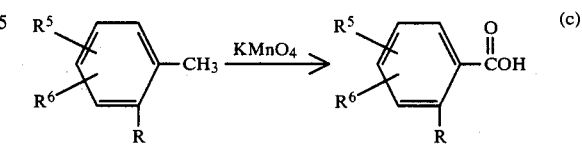

(c)

wherein R, $R^5$ and $R^6$ are as previously defined except that n is only zero and R is not alkyl.

In reaction (c) the substituted toluene is heated to reflux in an aqueous solution of potassium permanganate for several hours. The solution is then filtered and the reaction product is isolated by conventional techniques.

The requisite benzoyl cyanides can be prepared by the procedure of T.S. Oakwood and C.A. Weisgerber in *Organic Synthesis Coll.*, Vol. III, (E.C. Horning, editor) on pages 112–114, John Wiley and Sons, Inc. (1955).

The above described substituted benzoyl chlorides can be prepared from the corresponding substituted benzoic acids according to the teaching of *Reagents for Organic Synthesis*, Vol. I, L.F. Fieser and M Fieser, pp. 767–769 (1967).

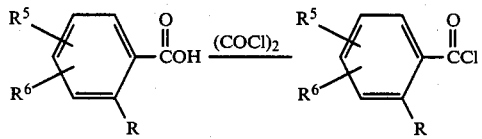

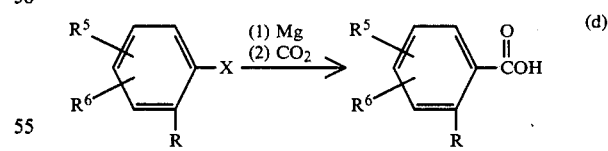

(d)

wherein R, $R^5$ and $R^6$ are as previously defined except that n is only zero; R is not cyano, nitro or halogen; and X is chlorine, bromine or chlorine.

In reaction (d) the substituted aromatic halide is allowed to react with magnesium in a solvent such as ether. The solution is then poured over crushed dry ice and the benzoic acid is isolated by conventional techniques.

wherein R, $R^5$ and $R^6$ are as previously defined, except that n is only zero.

The substituted benzoic acids can be prepared by a wide variety of general methods according to the teaching of *The Chemistry of Carboxylic Acids and Esters*, S. Patai, editor, J. Wiley and Sons, New York, N.Y. (1969) and *Survey of Organic Synthesis*, C.A. Buehler and D.F. Pearson, J. Wiley and Sons, (1970).

The following example teachs the synthesis of a representative compound of this invention.

EXAMPLE I 2-(2,4-Dichlorobenzoyl)-cyclopentane-1,3-dione

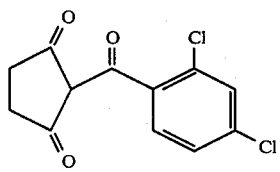

1,3-Cyclopentanedione [9.8 grams (g), 0.1 mole], 20.0 g (0.1 mole) 2,4-dichlorobenzoyl cyanide and 13.6 g (0.11 mole) anhydrous, powdered zinc chloride were combined in 100 milliliters (ml) methylene chloride. Triethylamine (10.1 g, 0.12 mole) was slowly added with cooling. The reaction mixture was stirred at room temperature for 5 hours and then poured into 2N hydrochloric acid. The aqueous phase was discarded and the organic phase was washed with 150 ml 5% $Na_2CO_3$ four times. The aqueous washings were combined and acidified with HCl, extracted with methylene chloride, dried and concentrated to yield 25.3 g of crude product. The crude product was dissolved in ether and stirred with 250 ml of 5% copper (II) acetate. The resulting copper salt was filtered, washed with ether and stirred with 6N hydrochloric acid to destroy the salt. The extract was washed with ether to yield 5.9 g of the desired product m.p. 109°–113° C. (21.7% yield). The structure was confirmed by instrumental analysis.

The following is a table of certain selected compounds that are preparable according to the procedure described hereto. Compound numbers are assigned to each compound and are used throughout the remainder of the application.

TABLE I

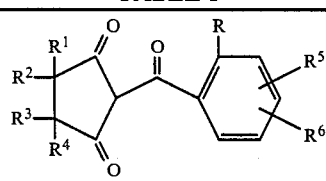

| Comp. No. | R | $R^1$ | $R^2$ | $R^3$ | $R^4$ | $R^5$ | $R^6$ | $n_D^{30}$ or m.p. °C. |
|---|---|---|---|---|---|---|---|---|
| 1[a] | Cl | H | H | H | H | H | 4-Cl | 109–113 |
| 2 | Br | H | H | H | H | H | H | oil |
| 3 | Cl | H | H | H | H | 3-Cl | 5-Cl | 103–108 |
| 4 | Cl | H | H | H | H | 3-Cl | 4-Cl | 99–114 |
| 5 | Cl | H | H | H | H | H | 4-SO$_2$CH$_3$ | semi-solid |
| 6[b] | NO$_2$ | H | H | H | H | H | H | 104–142 |

[a]Prepared in the example.
[b]Prepared by acetone cyanohydrin catalyzed rearrangement of the enol ester.

HERBICIDAL SCREENING TESTS

As previously mentioned, the herein described compounds produced in the above-described manner are phytotoxic compounds which are useful and valuable in controlling various plant species. Selected compounds of this invention were tested as herbicides in the following manner.

Pre-emergence herbicide test. On the day preceding treatment, seeds of eight different weed species are planted in loamy sand soil in individual rows using one species per row across the width of a flat. The weeds used are green foxtail (FT) (*Setaria viridis*), watergrass (WG) (*Echinochloa crusgalli*), wild oat (WO) (*Avena fatua*), annual morningglory (AMG) (*Ipomoea lacunosa*), velvetleaf (VL) (*Abutilon theophrasti*), Indian mustard (MD) (*Brassica juncea*), curly dock (CD) (*Rumex crispus*), and yellow nutsedge (YNG) (*Cyperus esculentus*). Ample seeds are planted to give about 20 to 40 seedlings per row, after emergence, depending upon the size of the plants.

Using an analytical balance, 600 milligrams (mg) of the compound to be tested are weighed out on a piece of glassine weighing paper. The paper and compound are placed in a 60 milliliter (ml) wide-mouth clear bottle and dissolved in 45 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monolaurate emulsifier to give a final solution of 0.5% (v/v). The solution is then sprayed on a seeded flat on a linear spray table calibrated to deliver 80 gallons per acre (748 L/ha). The application rate is 4 lb/acre (4.48 Kg/ha).

After treatment, the flats are placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

The results of the tests are shown in the following Table II.

TABLE II

| | Pre-Emergence Herbicidal Activity Application Rate - 4.48 kg/ha | | | | | | | |
|---|---|---|---|---|---|---|---|---|
| Cmpd. No. | FT | WG | WO | AMG | VL | NS | CD | YNG |
| 1 | 75 | 85 | 65 | 40 | 95 | 95 | 75 | 90 |
| 2 | 40 | 65 | 50 | 40 | 85 | 45 | 30 | 60 |
| 3 | 0 | 0 | 0 | 20 | 20 | 20 | 90 | 0 |
| 4 | 0 | 50 | 0 | 40 | 90 | 20 | 90 | 0 |
| 6 | 20 | 65 | 60 | 20 | 100 | 100 | 80 | 80 |

Post-Emergence Herbicide Test: This test is conducted in an identical manner to the testing procedure for the pre-emergence herbicide test, except the seeds of the eight different weed species are planted 10–12 days before treatment. Also, watering of the treated flats is confined to the soil surface and not to the foliage of the sprouted plants.

The results of the post-emergence herbicide test are reported in Table III.

TABLE III

| | Post-Emergence Herbicidal Activity Application Rate - 4.48 kg/ha | | | | | | | |
|---|---|---|---|---|---|---|---|---|
| Cmpd. No. | FT | WG | WO | AMG | VL | MD | CD | YNG |
| 1 | 80 | 95 | 90 | 95 | 100 | 100 | 90 | 80 |
| 2 | 95 | 85 | 90 | 65 | 85 | 100 | 100 | 20 |
| 3 | 0 | 0 | 0 | 30 | 100 | 80 | 90 | 80 |
| 4 | 30 | 20 | 30 | 0 | 0 | 0 | 40 | 0 |
| 6 | 100 | 70 | 100 | 95 | 100 | 100 | 70 | 25 |

The compounds of the present invention are useful as herbicides and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large partical size, as wettable powders, as emulsifiable concentrates, as powdery dusts, as solutions or as any several other known types of formulations, depending upon the desired mode of application. Preferred formulations for pre-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of the application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphthal, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite perlite and other organic or inorganic materials which absorb or which may be coated with the toxicant. Granular formulations normally are prepared to contain about 5% to about 25% of active ingredients which may include surface-active agents such heavy aromatic naphthas, kerosene or other petroleum fractions, or vegetable oils; and/or stickers such as destrins, glue or synthetic resins.

Typical wetting, dispersing or emulsifying agents used in agricultural formulations include, for example, the alkyl and alkylaryl sulfonates and sulfates and their sodium salts; polyhydric alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers and other herbicides, pesticides and the like. Fertilizers useful in combination with the active ingredients include, for example, ammonium nitrate, urea and superphosphate. Other useful additaments include materials in which plant organisms take root and grow such as compost, manure, humus, sand, and the like.

What is claimed is:

1. A compound of the formula

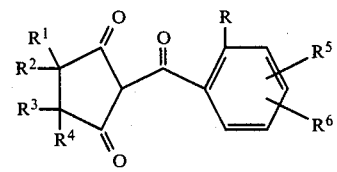

wherein
R is halogen; $C_1$–$C_4$ alkoxy; nitro; cyano; —S(O)$_n$R′ wherein n is the integer 0, 1, or 2, and R′ is $C_1$–$C_4$ alkyl; or R is is $C_1$-$C_4$ alkyl optionally substituted with halogen;

$R^1$ is hydrogen or $C_1$-$C_4$ alkyl;

$R^2$ is hydrogen, $C_1$-$C_4$ alkyl or

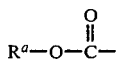

wherein $R^a$ is $C_1$-$C_4$ alkyl; or $R^1$ and $R^2$ together are alkylene having 3 to 6 carbon atoms;

$R^3$ is hydrogen or $C_1$-$C_4$ alkyl;

$R^4$ is hydrogen or $C_1$-$C_4$ alkyl;

$R^5$ and $R^6$ independently are (1) hydrogen; (2) halogen; (3) $C_1$-$C_4$ alkyl; (4) $C_1$-$C_4$ alkoxy; (5) $OCF_3$; (6) cyano; (7) nitro; (8) $C_1$-$C_4$ haloalkyl; (9) $R^bSO_n$— wherein n is the integer 0, 1, or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkyl or $C_1$-$C_4$ alkoxy; or (12) $SO_2NR^cR^d$ wherein $R^c$ and $R^d$ are as defined.

2. The compounds of claim 1 wherein R is chlorine, bromine, methoxy, nitro, cyano, $SO_2CH_3$, methyl, or $CF_3$; $R^1$ is hydrogen or methyl; $R^2$ is hydrogen or methyl; $R^3$ is hydrogen or methyl; $R^4$ is hydrogen or methyl; $R^5$ and $R^6$ independently are (1) hydrogen; (2) halogen; (3) $C_1$-$C_4$ alkyl; (4) $C_1$-$C_4$ alkoxy; (5) $OCF_3$; (6) cyano; (7) nitro; (8) $C_1$-$C_4$ haloalkyl; (9) $R^bSO_n$— wherein n is the integer 0, 1, or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkyl or $C_1$-$C_4$ alkoxy; or (12) $SO_2NR^cR^d$ wherein $R^c$ and $R^d$ are as defined.

3. The compounds of claim 2 wherein $R^5$ and $R^6$ are independently are hydrogen; chlorine; fluorine; bromine; methyl; methoxy; $OCF_3$; cyano; nitro, trifluoromethyl; $R^bSO_n$— wherein n is the integer 2 and $R^b$ is methyl, chloromethyl, trifluoromethyl, cyanomethyl, ethyl, or n-propyl; —$NR^cR^d$ wherein $R^c$ and $R^d$ independently are hydrogen or $C_1$-$C_4$ alkyl; $R^e$ C(O)— where $R^e$ is $C_1$-$C_4$ alkyl or $C_1$-$C_4$ alkoxy and $R^7$ is in the 3-position; or $SO_2NR^cR^d$ wherein $R^c$ and $R^d$ are as defined.

4. The compound of claim 2 wherein R is chlorine, bromine methoxy, nitro, methyl or $CF_3$; $R^5$ is hydrogen and $R^6$ is hydrogen, chlorine, bromine, fluorine, $CF_3$ or $R^bSO_2$ wherein $R^b$ is $C_1$-$C_4$ alkyl.

5. The compound of claim 2 wherein R is chlorine; $R^1$ is hydrogen; $R^2$ is hydrogen; $R^3$ is hydrogen; $R^4$ is hydrogen; $R^5$ is hydrogen; and $R^6$ is 4-chlorine.

6. The compound of claim 2 wherein R is bromine; $R^1$ is hydrogen; $R^2$ is hydrogen; $R^3$ is hydrogen; $R^4$ is hydrogen; $R^5$ is hydrogen; and $R^6$ is hydrogen.

7. The compound of claim 2 wherein R is nitro; $R^1$ is hydrogen; $R^2$ is hydrogen; $R^3$ is hydrogen; $R^4$ is hydrogen; $R^5$ is hydrogen; and $R^6$ is hydrogen.

8. The method of controlling undesirable vegetation comprising applying to the area where control is desired, an herbicidally effective amount of a compound having the formula

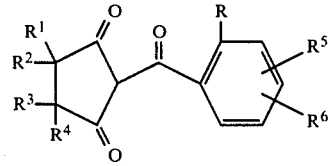

wherein
R is halogen; $C_1$-$C_4$ alkoxy; nitro; cyano; —$S(O)_nR'$ wherein n is the integer 0, 1, or 2, and R' is $C_1$-$C_4$ alkyl; or R is is $C_1$-$C_4$ alkyl optionally substituted with halogen;

$R^1$ is hydrogen or $C_1$-$C_4$ alkyl;

$R^2$ is hydrogen, $C_1$-$C_4$ alkyl or

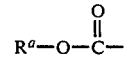

wherein $R^a$ is $C_1$-$C_4$ alkyl; or $R^1$ and $R^2$ together are alkylene having 3 to 6 carbon atoms;

$R^3$ is hydrogen or $C_1$-$C_4$ alkyl;

$R^4$ is hydrogen or $C_1$-$C_4$ alkyl;

$R^5$ and $R^6$ independently are (1) hydrogen; (2) halogen; (3) $C_1$-$C_4$ alkyl; (4) $C_1$-$C_4$; (5) $OCF_3$; (6) cyano; (7) nitro; (8) $C_1$-$C_4$ haloalkyl; (9) $R^bSO_n$— wherein n is the integer 0, 1, or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR_d$ wherein $R^c$ and $R^d$ independently are hydrogen or $C_1$-$C_4$ alkyl; (11) $R^eC(O)$— wherein $R^e$ is $C_1$-$C_4$ or $C_1$-$C_4$ alkoxy; or (12) $SO_2NR^cR^d$ wherein $R^c$ and $R^d$ are as defined.

9. The method of claim 8 wherein R is chlorine, bromine, methoxy, nitro, cyano, $SO_2CH_3$, methyl or $CF_3$; $R^1$: is hydrogen or methyl; $R^2$ is hydrogen or methyl; $R^3$ is hydrogen or methyl; $R^4$ is hydrogen or methyl; $R^5$ and $R^6$ independently are (1) hydrogen; (2) halogen; (3) $C_1$-$C_4$ alkyl; (4) $C_1$-$C_4$ alkoxy; (5) $OCF_3$; (6) cyano; (7) nitro; (8) $C_1$-$C_4$ haloalkyl; (9) $R^bSO_n$— wherein n is the integer 0, 1, or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkoxy; or (12) $SO_2NR^cR^d$ wherein $R^c$ and $R^d$ are as defined.

10. The method of claim 9 wherein $R^5$ and $R^6$ are independently are hydrogen; chlorine; fluorine; bromine; methyl; methoxy; $OCF_3$; cyano; nitro; trifluoromethyl; $R^bSO_n$— wherein n is the integer 2 and $R^b$ is methyl, chloromethyl, trifluoromethyl, cyanomethyl, ethyl, or n-propyl; —$NR^cR^d$ wherein $R^c$ and $R^d$ independently are hydrogen or $C_1$-$C_4$ alkyl; $R^eC(O)$— where $R^e$ is $C_1$-$C_4$ alkyl or $C_1$-$C_4$ alkoxy and $R^7$ is in the 3-position; or $SO_2NR^cR^d$ wherein $R^c$ and $R^d$ are as defined.

11. The method of claim 9 wherein R is chlorine, bromine, methoxy, nitro, methyl or $CF_3$; $R^5$ is hydrogen and $R^6$ is hydrogen; chlorine; bromine; fluorine; $CF_3$; or $R^2SO_2$ wherein $R^b$ is $C_1$-$C_4$ alkyl.

12. The method of claim 9 wherein R is chlorine; $R^1$ is hydrogen; $R^2$ is hydrogen; $R^3$ is hydrogen; $R^4$ is hydrogen; $R^5$; and $R^6$ is 4-chlorine.

13. The method of claim 9 wherein R is bromine; $R^1$ is hydrogen; $R^2$ is hydrogen; $R^3$ is hydrogen; $R^4$; $R^5$ is hydrogen; and $R^6$ is hydrogen.

14. The method of claim 8 wherein R is nitro; $R^1$ is hydrogen; $R^2$ is hydrogen; $R^3$ is hydrogen; $R^4$ is hydrogen; $R^5$ is hydrogen; and $R^6$ is hydrogen.

* * * * *